(12) United States Patent
Purohit et al.

(10) Patent No.: US 12,357,158 B2
(45) Date of Patent: Jul. 15, 2025

(54) MEDICAL DEVICES AND RELATED METHODS THEREOF

(71) Applicant: Boston Scientific Medical Device Limited, Galway (IE)

(72) Inventors: Hitendra Purohit, Gurgaon (IN); Deepak Kumar Sharma, Gurgaon (IN); Madhurima Debnath, Gurgaon (IN)

(73) Assignee: Boston Scientific Medical Device Limited, Galway (IE)

( * ) Notice: Subject to any disclaimer, the term of this patent is extended or adjusted under 35 U.S.C. 154(b) by 170 days.

(21) Appl. No.: 17/810,963

(22) Filed: Jul. 6, 2022

(65) Prior Publication Data

US 2023/0020816 A1     Jan. 19, 2023

Related U.S. Application Data

(60) Provisional application No. 63/203,215, filed on Jul. 13, 2021.

(51) Int. Cl.
*A61B 1/00* (2006.01)
*A61B 1/05* (2006.01)

(52) U.S. Cl.
CPC ...... *A61B 1/00183* (2013.01); *A61B 1/00082* (2013.01); *A61B 1/00101* (2013.01); *A61B 1/00119* (2013.01); *A61B 1/00148* (2022.02); *A61B 1/053* (2013.01)

(58) Field of Classification Search
CPC ............ A61B 1/00183; A61B 1/00148; A61B 1/00082; A61B 1/00101; A61B 1/00109; A61B 1/053; A61B 1/00177; A61B 1/015; A61B 1/00137; A61B 1/012; A61B 1/00181; A61B 1/00147; A61B 1/01; A61B 1/0014
See application file for complete search history.

(56) References Cited

U.S. PATENT DOCUMENTS

| | | | |
|---|---|---|---|
| 5,217,001 A * | 6/1993 | Nakao | A61B 1/00135 600/116 |
| 9,226,648 B2 * | 1/2016 | Saadat | A61B 1/00085 |
| 2003/0135122 A1 * | 7/2003 | Bambot | A61B 5/4312 600/476 |
| 2006/0264707 A1 | 11/2006 | Kinney | |

(Continued)

FOREIGN PATENT DOCUMENTS

| | | | |
|---|---|---|---|
| CN | 108992144 A | 12/2018 | |
| WO | WO-2009144729 A1 * | 12/2009 | ............... A61B 1/04 |

(Continued)

*Primary Examiner* — Michael J Carey
*Assistant Examiner* — Timothy Tuan Luu
(74) *Attorney, Agent, or Firm* — Bookoff McAndrews, PLLC (57) ABSTRACT

A medical device comprising a handle, a shaft extending from the handle, and an inflatable module at a distal portion of the shaft, the module including a camera, wherein the shaft includes a body defining a first channel extending between a first end configured to be in fluid communication with a fluid source, and a second end in fluid communication with the module, and wherein inflation of the module alters a viewing angle of the camera relative to an axis of the distal portion of the shaft.

17 Claims, 5 Drawing Sheets

(56) References Cited

U.S. PATENT DOCUMENTS

| | | | |
|---|---|---|---|
| 2009/0023998 A1* | 1/2009 | Ratnakar | A61B 1/00105 600/121 |
| 2010/0010298 A1 | 1/2010 | Bakos et al. | |
| 2015/0327754 A1* | 11/2015 | Leeflang | A61B 1/128 600/109 |
| 2020/0329953 A1 | 10/2020 | Truckai | |
| 2022/0095901 A1* | 3/2022 | Flanagan | A61B 1/00082 |

FOREIGN PATENT DOCUMENTS

| | | | | |
|---|---|---|---|---|
| WO | WO-2015122474 A1 * | 8/2015 | | A61B 1/00135 |
| WO | WO-2017087549 A1 * | 5/2017 | | A61B 1/00009 |

* cited by examiner

MEDICAL DEVICES AND RELATED METHODS THEREOF

CROSS-REFERENCE TO RELATED APPLICATION(S)

This application claims the benefit of priority from U.S. Provisional Application No. 63/203,215, filed on Jul. 13, 2021, which is incorporated by reference herein in its entirety.

TECHNICAL FIELD

This disclosure relates generally to medical devices. More particularly, at least some embodiments of the disclosure relate to medical scopes for imaging and/or therapeutic purposes during endoscopic procedures.

BACKGROUND

Endoscopic procedures include a number of varying procedures, e.g., upper endoscopy, gastroscopy, colonoscopy, endoscopic retrograde cholangiopancreatography (ERCP), etc., each of which involves imaging and/or treatment of different bodily openings and lumens. Therefore, each procedure requires the use of a specific scope, each having dimensions, e.g., shaft diameter, working length, etc., that are suited for traversing specific bodily openings and lumens, e.g., upper GI tract, colon. As a result, this may require a number of different scopes for the different types of endoscopic procedures, which may be costly.

SUMMARY OF THE DISCLOSURE

According to an example, a medical device may comprises a handle, a shaft extending from the handle, and an inflatable module at a distal portion of the shaft, the module including a camera, wherein the shaft includes a body defining a first channel extending between a first end configured to be in fluid communication with a fluid source, and a second end in fluid communication with the module, and wherein inflation of the module alters a viewing angle of the camera relative to an axis of the distal portion of the shaft.

In another example, the body of the shaft may further define at least one inflatable second channel extending between a first end configured to be in fluid communication with a second fluid source and a sealed second end, so that the at least one second channel increasingly protrudes radially outwards, relative to an adjacent exterior surface of the body, when inflated from a deflated state. The at least one inflatable second channel may include a plurality of second channels, wherein the plurality of second channels are circumferentially arranged around the body of the shaft. The first channel may include a default, deflated state. The first channel and the at least one second channel may be tubular structures extending longitudinally along an exterior of the body. The inflatable module may be ring-shaped and coupled around the distal portion of the shaft. The inflatable module may be coupled to the shaft so that the inflatable module hinges about a distal end of the inflatable module as the inflatable module is inflated. The inflatable module may include a default, deflated state, in which a camera viewing angle is perpendicular to the axis of the distal portion of the shaft, and an inflated state in which a camera viewing is parallel to the axis of the distal portion of the shaft. The inflatable module may further include a partially-inflated state, in which the camera viewing angle is at an angle between the camera viewing angle in the default, deflated state and the camera viewing angle in the inflated state. The medical device may further comprise a first intermediary hub including a first end and a second end, wherein the first end is configured to be coupled to a fluid source and the second end is configured to be coupled to the first end of the first channel. The medical device may further comprise a second intermediary hub including a first end configured to be coupled to the second fluid source and a second end in fluid communication with the at least one second channel. The medical device may further comprise a ring coupled to a proximal portion of the shaft, wherein the ring is translatable along the shaft when a force is applied by a user. The ring may protrude radially outwards relative to an exterior of the body of the shaft, and the ring frictionally engages the shaft to inhibit insertion of the shaft past the ring when inserting the shaft into an opening. The distal portion of the at least one second channel may include an enlarged portion that inflates to a cross-sectional dimension larger than a cross-sectional dimension of inflatable portions of the at least one second channel adjacent to the enlarged portion. The inflatable module may be removable from the distal portion of the shaft.

According to an example, a medical device may comprise a shaft, and an inflatable module at a distal portion of the shaft, the module including a camera, wherein the shaft includes a body defining a central lumen, a first channel, and a second channel, wherein the first channel extends between a first end configured to be in fluid communication with a first fluid source, and a second end in fluid communication with the module such that providing fluid from the first fluid source inflates the module, altering a viewing angle of the camera relative to an axis of the distal portion of the shaft, and wherein the second channel extends between a first end configured to be in fluid communication with a second fluid source and a closed second end so that the second channel is inflatable to increase an outer diameter of the shaft. The body of the shaft may further define a third channel, the third channel extending between a first end configured to be in fluid communication with a third fluid source and a closed second end so that the third channel is inflatable. The third channel may be inflatable so that the third channel protrudes radially inwards relative to portions of the central lumen adjacent to the third channel, thereby decreasing a cross-sectional dimension of the central lumen.

According to an example, a medical device may comprise a handle, a shaft extending from the handle, and an inflatable module coupled at a distal portion of the shaft, the module including a camera, wherein the shaft includes a first channel, a working channel, and an inflatable annular channel surrounding the working channel, wherein the first channel extends between a first end configured to be in fluid communication with a first fluid source, and a second end in fluid communication with the module, and wherein the inflatable annular channel extends between a first end configured to be in fluid communication with a second fluid source and a sealed second end. The inflatable annular channel may be defined by a sheath encapsulating at least a portion of the shaft.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to aspects of the disclosure, examples of which are illustrated in the accompanying drawings. Wherever possible, the same or similar reference numbers will be used through the drawings to refer to the same or like parts. The term "distal" refers to a location or portion of a medical device farthest away from a user of the device, e.g., when introducing a device into a subject (e.g., patient). By contrast, the term "proximal" refers to a location or portion closest to the user, e.g., when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

This disclosure may solve one or more of the limitations in the art. The scope of the disclosure, however, is defined by the attached claims and not the ability to solve a specific problem. Embodiments of this disclosure include devices and methods for endoscopic procedures. Exemplary devices include a medical scope, e.g., an endoscope. Said medical scope may include a handle, a shaft, a stopper, and an imaging module coupled to a distal portion of said shaft. The handle is not particularly limited and may be any suitable medical scope handle. For example, the handle may include at least one actuator, e.g., steering knobs, controller, configured to maneuver or adjust a distal portion of the shaft pneumatically or via mechanical means, e.g., steering cables, and at least one port configured to receive a medical device, e.g., an accessory device, allowing said medical device to extend distally through a working channel of said shaft. A distal portion of the handle may be detachably or fixedly coupled to a proximal end of said shaft. For example, a distal end of the handle may be detachable from a disposable shaft, so that the shaft may be disposed of after usage, and the handle may be re-used. In some exemplary embodiments, the detachable handles may vary in length to accommodate for different types of endoscopic procedures (e.g., upper GI, colonoscopy, ERCP). Thus, a user may select a scope of a suitable length, depending on the type of procedure, and may couple said scope to the universal shaft, which is discussed in further detail below.

Said shaft may include a longitudinal body extending between a proximal end and a distal end. The length of the longitudinal body is not particularly limited, and may be any suitable length, e.g., approximately 1 meter to 3 meters. However, it is noted that a working length of the shaft, i.e., the maximum length which may enter a bodily lumen, may be adjustable, as discussed in further detail below. Due to such adjustability in length, said shaft may be suitable for bodily lumens of various lengths. The material of said shaft body is not particularly limited, and may be of any suitable flexible material, e.g., polytetrafluoroethylene (PTFE). Said shaft body may define at least one central lumen extending between the proximal end and the distal end of the shaft, e.g., the working channel of the shaft. The dimensions of the at least one central lumen are not particularly limited, e.g., a diameter between 1 mm to 5 mm, a diameter of 4.2 mm, 3.7 mm, 2.8 mm, etc., and in some examples, may be adjustable as discussed when referring to FIGS. 4A-4B.

The shaft body may further define at least one first channel and at least one second channel. The number of first channels and the number of second channels is not particularly limited. Both the first channel and the second channel may extend longitudinally along a radially outer surface of the body, thereby defining at least a portion of the outer surface of the shaft and the outer diameter of the shaft. The outer diameter of the shaft may be approximately 7 mm to 15 mm, e.g., at least 9 mm, 9.9 mm, 11.3 mm, 12.8 mm, etc. Moreover, the first channel and the second channel may be circumferentially arranged along the outer surface, e.g., on radially opposite sides of the shaft. The shape of the first channel and the second channel is not particularly limited, e.g., tubular, sleeve, sheath, etc., and the dimensions are not particularly limited as well. The first channel may be configured to provide passage for material or fluid to travel from a first hub (discussed further below) to the imaging module, thereby inflating the module. The second channel may be inflatable from a default, deflated state via a second hub (discussed further below), thereby radially expanding the second channel and adjusting the outer diameter of the shaft. Thus, the shaft may be utilized in a number of endoscopic procedures, e.g., colonoscopy, upper endoscopy, ERCP, etc., regardless of the dimensions of the bodily opening and lumen, as the outer diameter of the shaft may be adjusted accordingly. Such a universal shaft may address the need for a number of different shafts for each endoscopic procedure. Both the first channel and the second channel are discussed in further detail below.

The shaft may further include at least one first hub and at least one second hub. The first hub and the second hub may be located along a proximal portion of the shaft, and may respectively be in fluid/material communication with the first channel and the second channel. The first hub is not particularly limited and may be any suitable port/medium that receives fluid/material from a fluid/material source, e.g., $CO_2$, saline, water, etc., and delivers fluid/material distally to the first channel, thereby inflating the distal imaging module. Likewise, the second hub is not particularly limited and may be any suitable port/medium that receives fluid/material from the same or different fluid/material source and delivers fluid/material to the second channel, thereby inflating the second channel and adjusting the outer diameter of the shaft. Both the first hub and second hub may include a control means, e.g., a valve, switch, etc., by which the volume of fluid/material delivery or release may be adjusted. Moreover, the number of first hubs and second hubs is not particularly limited, and does not necessarily correspond to the number of first channels and second channels. For example, one second hub may be in fluid/material communication with a plurality of second channels. In another example, each second channel may be in fluid/material communication with its corresponding second hub.

The medical device may also include a stopper coupled to a proximal portion of the shaft. The stopper may be any suitable clip, ring, or like component. The stopper may engage the shaft, e.g., frictionally, so that the stopper may be translatable along the length of the shaft by a user, but also maintain its position along the shaft when released by the user. The stopper may protrude radially outwards relative to the outer surface of the shaft. The stopper may protrude such that the outer diameter of the stopper is larger than a diameter of an opening, e.g., bodily opening, mouthguard opening, etc., leading to the bodily lumen. Therefore, the protruding aspects of said stopper may inhibit further insertion of the shaft into an opening beyond the proximal stopper, due to the engagement between the stopper and surfaces surrounding the body opening. Thus, the translatable stopper may be a means for adjusting a working length of the shaft. For example, the working length of the shaft may be lengthened by translating the stopper proximally along the shaft, relative to its starting position. Alternatively, the working length of the shaft may be shortened by translating the stopper distally along the shaft, relative to its starting position. The working length of the shaft may be adjusted to certain lengths, e.g., approximately 1 meter to 2 meters, 1.03 meters, 1.24 meters, 1.33-1.68 meters, etc., to accommodate for different types of endoscopic procedures. Thus, the shaft may be utilized in a number of endoscopic procedures regardless of the dimensions of the bodily opening and lumen, as the working length of the shaft may also be adjusted accordingly.

The adjustability of each of the outer diameter and the length of the shaft may provide a cost-savings effect in that the above-described universal shaft may eliminate the need for a variety of different shafts for different types of anatomies and procedures. Furthermore, the adjustability of the dimensions of the shaft to shaft dimensions that are clinically used for certain procedures, e.g., colonoscopy, bronchoscopy, etc., may provide familiarity to operators of the shaft. In addition, a universal, adjustable shaft may also be clinically advantageous in comparison to a shaft having a static outer diameter and length but viable in different anatomies for different procedures. This is because the adjustable shaft may adjust its outer diameter and length to provide optimal dimensions for each of the anatomies of different procedures. Such dimensions, e.g., an outer diameter and a length, may provide a desirable level of torqueability and stability of the shaft within the respective bodily lumen of the procedure, e.g., stomach, colon, etc. Moreover, such dimensions may also minimize undesirable effects, e.g., kinking and looping of the shaft within a bodily lumen, which may occur during the insertion of a shaft having an outer diameter too small in comparison to the surrounding bodily lumen.

As noted above, the imaging module may be coupled to a distal portion of the shaft. The module may include a body, at least one camera coupled to a radially outer-facing surface of the body, and at least one light source coupled to a radially outer-facing surface of the body. The body of the module may be any suitable shape, e.g., ring-shaped, and may be coupled to the distal portion of the shaft via any suitable means, e.g., adhesive, molding, mechanical means, etc. The body of the module may comprise any suitable inflatable material, and is not particularly limited. Moreover, the body may be in fluid/material communication with a fluid/material source, via at least one first channel. Thus, the module may be inflatable from a default, deflated state to an inflated state. In some embodiments, only a distal portion of the body of the module may be coupled to the shaft so that the module hinges about said coupled portion as the module is inflated from the default, deflated state. As a result, the at least one camera and the at least one light source may transition from a side viewing camera/light source when the module is in its default, deflated state, to a front viewing camera/light source when the module is inflated. Such a functionality may allow for said shaft to be utilized in endoscopic procedures requiring a side viewing imaging module and also procedures requiring a front viewing imaging module. It is noted that the particular camera and the particular light source is not limited and they may be coupled to a remainder of the imaging module via any suitable means, e.g., adhesive, molding, etc. Moreover, any cables and wirings of the camera and light sources may extend proximally through the aforementioned central lumen of the shaft, and towards a suitable electrical/imaging/light source. It is further noted that the imaging module may be detachable from a distal portion of the shaft, thereby allowing for the re-usability of the imaging module.

The aforementioned features of the medical device are further discussed when referring to the figures.

Figure 1:
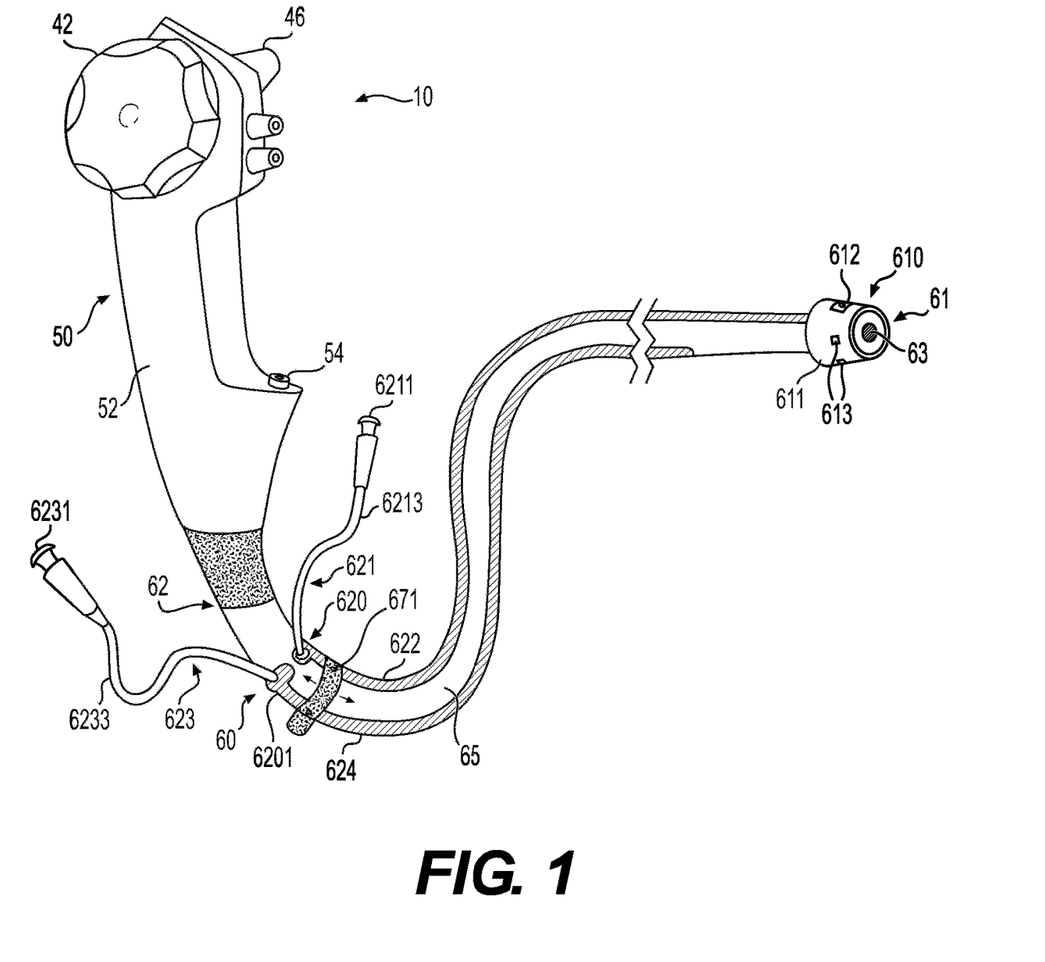
FIG. 1 is a perspective view of a medical device, according to some aspects of the disclosure.

Referring to FIG. 1, an exemplary medical device 10, e.g., an endoscope, includes a handle 50, a shaft 60 connected at a distal end of handle 50, a stopper 671 coupled to a proximal portion of shaft 60, and an imaging module 610 coupled to a distal portion of shaft 60. Handle 50 may be configured for actuating or otherwise controlling features of medical device 10 and/or one or more accessory tools or devices associated with medical device 10. Handle 50 as shown includes an actuator 42, which controls articulation of shaft 60, e.g., an articulation joint at or proximate a distal end 61 of shaft 60. For example, the actuator 42 may control movement of the shaft 60 in multiple directions, e.g., movement along different planes. Actuator 42 may include, for example, at least one rotatable knob that rotates to push/pull cables or wires coupled to shaft 60. For example, one or more cables or wires, e.g., two, three, four, etc., may comprise medical grade plastic or metal, and may extend distally from a respective knob of actuator 42 to connect to flexible shaft 60 to control movement thereof. Distal ends of the cables or wires may extend through shaft 60 and terminate at an articulation joint and/or a distal tip 61 of shaft 60. For example, one or more cables or wires may be connected to an articulation joint, and rotation of actuator 42 may control the cables or wires to move the articulation joint and/or the distal end of shaft 60, e.g., along multiple directions. According to some aspects of the present disclosure, one or more electrical cables (not shown) may extend from the proximal end of device 10 (and from an electrical source) to imaging module 610 and may provide electrical controls to a camera 612, a light source 613, and/or other electronics at module 610. Electrical cables may carry imaging signals received at camera 612 to be processed and/or displayed on a display. Device 10 may also include at least one port, e.g., port 54 for introducing an accessory device or tool.

Shaft 60 includes a tubular body 65 extending between distal end 61 and a proximal end 62 which is connected to the distal end of the handle 50. Body 65 defines a central lumen 63, which may serve as a working channel for accessory devices and tools to extend therethrough from port 54. As previously discussed, the dimensions of central lumen 63, e.g., the diameter, is not particularly limited.

Figure 2A:
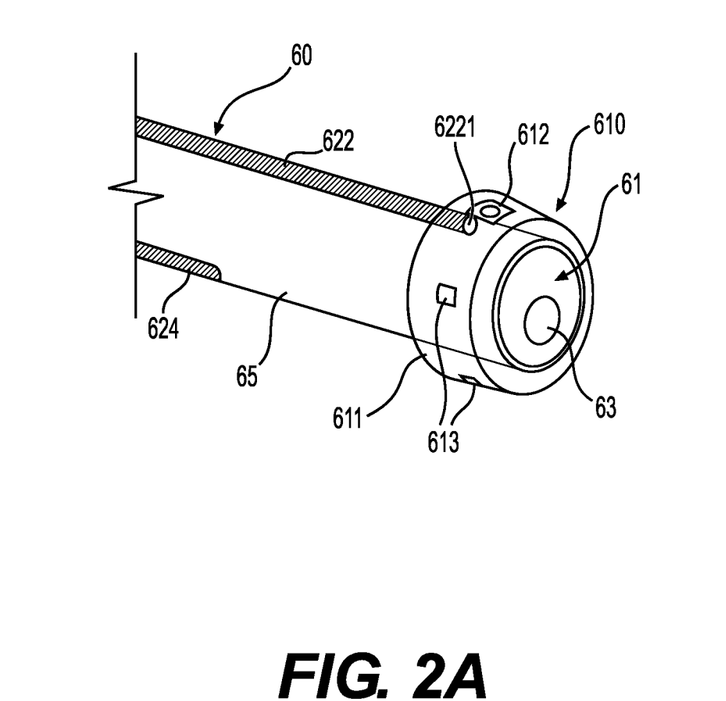
FIGS. 2A-2B are perspective views of a portion of the medical device of FIG. 1.
Figure 2B:
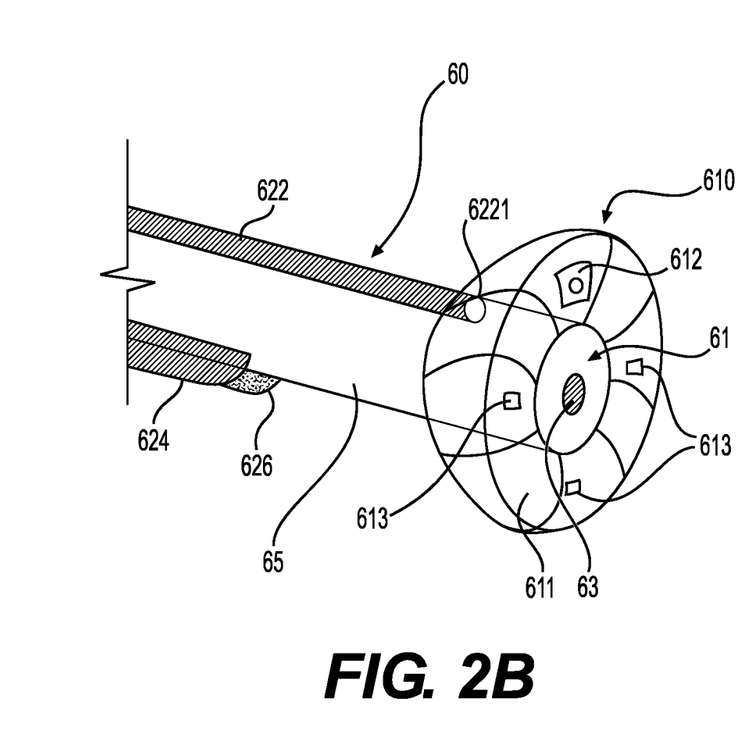

In addition to central lumen 63, body 65 further defines a first channel 622 and second channels 624 and 626 (channel 626 shown in FIG. 2B). First channel 622 and second channels 624 and 626 are arranged circumferentially along body 65. The degree of separation between each of the aforementioned channels is not particularly limited.

Referring to FIGS. 1, 2A, and 2B, first channel 622 is a tubular channel extending longitudinally along an outer surface of body 65. First channel 622 includes a proximal opening (not shown) coupled to and in fluid/material communication with a first hub 621, and a distal opening 6221 (shown in FIG. 2A) coupled to and in fluid/material communication with imaging module 610. Thus, first channel 622 may provide a passage of fluid/material to module 610. First channel 622 may be attached to, or integrated with, said outer surface of body 65, thereby defining at least a portion of the outer surface and the diameter of shaft 60. The means by which channel 622 may be attached to or integrated with body 65 is not particularly limited, e.g., adhesives, overmolding. It is noted that shaft 60 includes only one first channel 622, but other exemplary shaft embodiments may include a plurality of first channels 622.

Second channels 624 and 626 are also tubular channels extending longitudinally along an outer surface of body 65. Second channels 624 and 626 each includes a proximal opening (not shown) in fluid/material communication with a second hub 623, and a closed distal end (shown in FIG. 2B). Thus, channels 624 and 626 may be enclosed channels configured to receive fluid/material, via second hub 623, and to inflate from a default, deflated state (shown in FIG. 2A). Second channels 624, 626 may be any suitable compliant or non-compliant balloon or balloon-like structure, and may comprise any suitable inflatable material. Second channels 624 and 626 may be attached to, or integrated with, said outer surface of body 65, thereby defining at least a portion of the outer surface and the outer diameter of shaft 60. Thus, when channels 624 and 626 receive fluid/material and inflate, the outer diameter of shaft 60 may increase from a default diameter, e.g., any of the diameter discussed in this disclosure, to an adjusted diameter, as channels 624 and 626 increasingly protrude radially outwards relative to the outer surface of body 65 (shown in FIG. 2B). The means by which channels 624 and 626 may be attached to or integrated with body 65 is not particularly limited, e.g., adhesives, overmolding. It is noted that the closed distal ends of channels 624 and 626 are proximal of distal end 61 of shaft 60. This is to minimize any possible hindrance to the articulation/maneuverability of the distal portion of shaft 60 by the inflation of channels 624, 626. Moreover, it is noted that shaft 60 includes two second channels 624 and 626, but other exemplary shaft embodiments may include only one second channel or additional second channels along shaft 60.

In addition to body 65, shaft 60 further includes first hub 621 and second hub 623. As shown in FIG. 1, both first hub 621 and second hub 623 are positioned on a proximal portion of body 65. First hub 621 includes a port 6211 and a channel 6213. Port 6211 includes a first end including an opening (not shown) configured to couple with a fluid/material source and a second end coupled to channel 6213. Channel 6213 includes a first end coupled to the second end of port 6211 and a second end in fluid communication with first channel 622. As shown in FIG. 1, the second end of channel 6213 may be coupled to the proximal opening of channel 622. However, in other exemplary embodiments, said second end of channel 6213 may be coupled to an intermediate multi-lumen feature, e.g., a ring lumen, which in turn may be coupled to a proximal opening(s) of at least one first channel 622. Thus, a proximal fluid/material source and port 6211 may be in fluid/material communication with module 610, via first channel 622 and hub channel 6213.

Similarly, second hub 623 includes a port 6231 and a channel 6233. Port 6231 includes a first end including an opening (not shown) configured to couple with a fluid/material source and a second end coupled to channel 6233. Channel 6233 includes a first end coupled to the second end of port 6231 and a second end in fluid communication with second channels 624 and 626. To be in fluid/material communication with both channels 624 and 626, said second end of channel 6233 may be coupled to an intermediary ring lumen 6201 circumferentially wrapping around at least a portion of body 65, which in turn is in fluid/material communication with both second channel 624 (as shown in FIG. 1) and second channel 626. Second channels 624, 626 may be attached to ring lumen 6201 or integrated with ring lumen 6201 as shown in FIG. 1. Thus, a proximal fluid/material source and port 6231 may be in fluid/material communication with second channels 624, 626, via ring lumen 6201 and hub channel 6233.

As shown in FIG. 1, stopper ring 671 is coupled to a proximal portion of shaft 60—a portion of shaft 60 that is distal to hubs 621 and 623. Stopper ring 671 may surround and frictionally engage shaft 60, including shaft body 65 and second channels 622 and 624, so that ring 671 may be translatable along the length of shaft 60, as indicated by the directional arrows. However, given the frictional engagement between an inner surface (not shown) of ring 671 and the outer surface of body 65 and channels 622 and 624, ring 671 may maintain its position along shaft 60 until a sufficient degree of force is applied against ring 671. It is noted that ring 671 is configured to not interfere with the inflation of channels 622 and 624. For example, ring 671 may also be of a flexible, adjustable material so as to expand with or be adjusted to the expanded outer diameter of shaft 60 when channels 622 and 624 are inflated. Stopper ring 671 protrudes radially outwards relative to the outer surface of shaft 60. Thus, ring 671 inhibits further insertion of shaft 60 into a body lumen, past ring 671, thereby defining a working length (i.e., insertable length) of shaft 60. Thus, as previously noted, ring 671 may be translatable along the length of shaft 60 to adjust a working length of shaft 60 to accommodate for various types of bodily lumens.

Figure 3A:
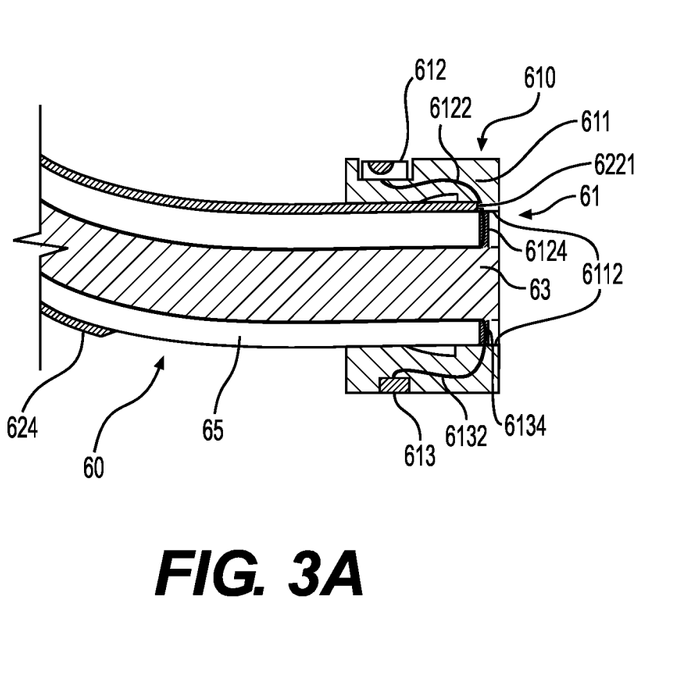
FIGS. 3A-3B are cross-sectional views of a portion of the medical device of FIG. 1.
Figure 3B:
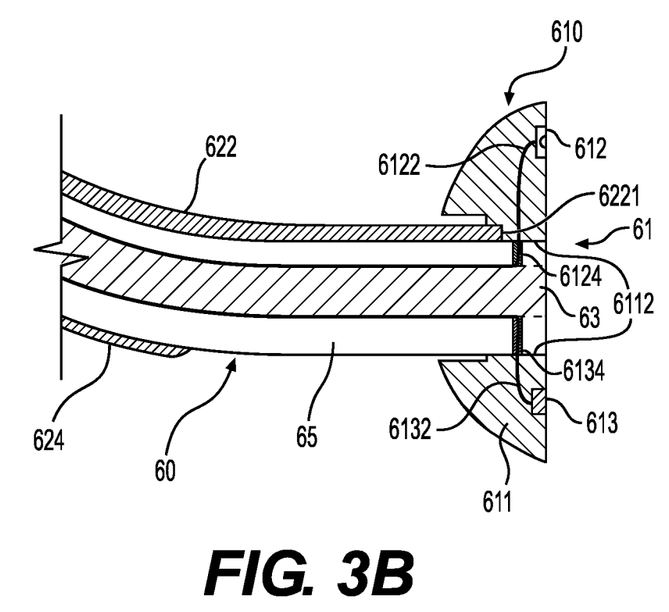

Referring to FIGS. 1-3B, an exemplary imaging module 610 includes an inflatable body 611, a camera 612 coupled to body 611, and lights 613 also coupled to body 611. Body 611 is a ring-shaped body surrounding a distal portion of shaft 60. As previously discussed, body 611 may be in fluid communication with distal opening 6221 of first channel 622, as shown in FIGS. 2A-2B. Thus, body 611 may receive fluid/material from a fluid/material source, via first channel 622, and transition from a default, deflated state (shown in FIG. 2A, 3A) to an inflated state (shown in FIGS. 2B, 3B). It is noted that a distal inner surface 6112 of ring body 611 may be detachably or fixedly coupled to the outer surface of shaft 60 via any suitable means. As a result of such coupling, body 611 hinges about said coupled portion (shown in FIGS. 3A-3B) as module 610 is inflated from the default, deflated state. Camera 612 is not particularly limited, e.g., CMOS, CCO, etc., and is embedded/coupled to an outer-facing surface of body 611 via any suitable means, e.g., adhesives. Likewise, lights 613 are not particularly limited, e.g., LED, and are also embedded/coupled to an outer-facing surface of body 611 via any suitable means. Camera 612 and lights 613 may be connected to a controller (not shown) via a wireless or wired connection. For example, both camera 612 and lights 613 may be wired to a proximal controller and/or source (not shown), as shown in FIGS. 3A-3B. A wire 6122 is coupled to and extends proximally from camera 612, via lumen 63. Wire 6122 extends to lumen 63 via a passage 6124 at a distal portion of shaft body 65, passage 6124 providing a passageway from a cavity of body 611 to a distal portion of lumen 63. Wire 6122 may extend proximally through lumen 63 while attached to the inner surface of body 65 defining lumen 63, thereby keeping wire 6122 from obstructing the passage of accessory devices via lumen 63. Similarly, a wire 6132 is coupled to and extends proximally from lights 613. Wire 6132 also extends to lumen 63 via a passage 6134 at a distal portion of shaft body 65, passage 6134 providing a passageway from a cavity of body 611 to a distal portion of lumen 63. Wire 6132 may also extend proximally through lumen 63 while attached to the inner surface of body 65 defining lumen 63. As an alternative to passage through lumen 63, wires 6122, 6132 may extend through shaft 65 via a discrete lumen dedicated to wires 6122, 6132.

The relative positioning of camera 612 and lights 613 on said outer-facing surface of body 611 is not particularly limited. Notably, camera 612 and lights 613 may be positioned on body 611 so that the aforementioned hinging of body 611 transitions camera 612 and lights 613 from side viewing (shown in FIG. 3A) to front viewing (shown in FIG. 3B). Imaging module 610 is not limited to only a side viewing state and a front viewing state. Body 611 may also be partially inflated to various degrees so that camera 612 may be at other angles relative to the axis of shaft 60. Thus, camera 612 may be approximately perpendicular to shaft 60, e.g., a side viewing state, parallel to shaft 60, e.g., a front viewing state, as well as at all angles in between.

Referring to FIGS. 1A-3A, an example of how medical device 10 may be used is further discussed below. A user may first determine the type of endoscopic procedure and/or the bodily lumen to be traversed via device 10. Based on such determination, the user may either maintain shaft 60 in its default diameter, or adjust the diameter of shaft 60 via inflation of second channels 624, 626 so that shaft 60 is of an appropriate diameter. To inflate channels 624, 626, the user may, for example, turn on a fluid/material source coupled to second hub 623, so that said fluid/material may pass through second hub 623, ring lumen 6201, and flow into channels 624, 626. The degree of inflation of channels 624, 626 may be adjusted via any suitable means, e.g., valves/switches on hub 623 and/or the fluid/material source. Once shaft 60 is adjusted to the appropriate diameter, the user may also adjust the working length of shaft 60 by translating stopper ring 671 along a length of body 65 of shaft 60. It is noted that the working length of shaft 60 may also be adjusted prior to the inflation of channels 624, 626. After adjustment of the outer diameter and the working length of shaft 60, the user may deliver a distal end of shaft 60 into the body of a subject, e.g., via the natural orifice, e.g., a mouth or anus, and through the tortuous natural body lumen of the subject, e.g., an esophagus, stomach, colon, etc., in accordance with the determined endoscopic procedure, towards a targeted site. Once delivered to the targeted site, the user may either maintain imaging module 610 in its default, side viewing state, transition imaging module 610 to its front viewing state, or apply an appropriate level of inflation to achieve any desired camera viewing angle between the side viewing state and the front viewing state. To transition module 610 to its front viewing state (or any intermediate viewing state), the user may, for example, turn on a fluid/material source coupled to first hub 621, so that said fluid/material may pass through first hub 621, first channel 622, and flow into inflatable body 611 of module 610.

Figure 4:
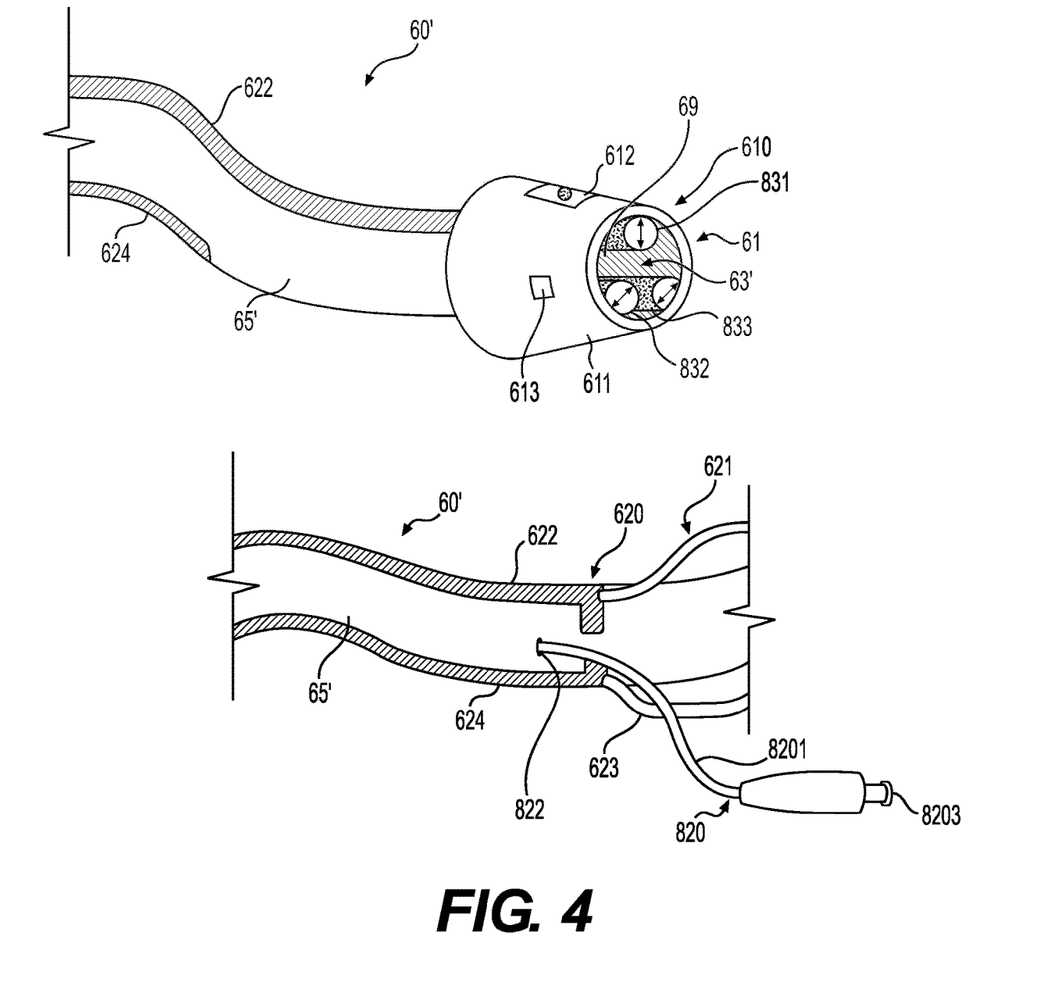
FIG. 4 is a perspective view of a portion of another medical device, according to some aspects of the disclosure.

In addition to adjustable outer diameter and working length features, an exemplary shaft embodiment may also include features which may allow for a diameter of the shaft working channel to be adjusted. FIG. 4 illustrates such an exemplary shaft 60'. Shaft 60' is similar to shaft 60 in some respects, and like reference numerals refer to like parts. Shaft 60' includes body 65' and a third hub 820. Body 65', unlike body 65, further includes inner channels 831, 832, 833 extending longitudinally along an inner surface 69 of body 65', thereby defining at least a portion of inner surface 69 and the diameter of central lumen 63'. Inner channels 831, 832, 833 each includes a proximal opening (not shown) in fluid/material communication with a third hub 820, and a closed distal end. Thus, channels 831, 832, 833 may be enclosed channels configured to receive fluid/material, via third hub 820, and to inflate from a default, deflated state. Inner channels 831, 832, 833 may be attached to, or integrated with, inner surface 69 of body 65'. Thus, when channels 831, 832, 833 receive fluid/material and inflate, the diameter lumen 63' may decrease from a default diameter, e.g., approximately 3 to 5 mm (such as 4.2 mm), to an adjusted diameter, e.g., approximately 2 to 4 mm (such as 3.7 mm, 2.8 mm, etc.), as channels 831, 832, 833 increasingly protrude radially inwards relative to the inner surface 69 of body 65' (indicated by the directional arrows shown in FIG. 4). The means by which channels 831, 832, 833 may be attached to or integrated with body 65' is not particularly limited, e.g., adhesives, overmolding. Moreover, it is noted that body 65' includes three inner channels 831, 832, 833, but other exemplary shaft embodiments may include only one or two inner channel(s) or additional inner channels.

The adjustability of a diameter of the shaft working channel may be clinically advantageous. For example, the working channel may be adjusted to a smaller diameter when using accessory devices or tools typically used in conjunction with shafts having smaller working channel diameters, relative to the default diameter of shaft 60'. Thus, adjusting a diameter of the working channel of shaft 60' to accommodate for such accessory devices or tools may minimize undesirable effects, e.g., kinking of the accessory device, that may result from the use of accessory devices in larger working channels.

Third hub 820 includes a port 8203 and a channel 8201. Port 8203 includes a first end including an opening (not shown) configured to couple with a fluid/material source and a second end coupled to channel 8201. Channel 8201 includes a first end coupled to the second end of port 8203. As shown in FIG. 4, channel 8201 may enter body 65', via an opening 822 to central lumen 63' so that a second end of channel may be in fluid/material communication with inner channels 831, 832, 833. To be in fluid/material communication with multiple inner channels 831, 832, 833, said second end of channel 8201 may be coupled to an inner ring lumen (or like feature) lined/attached to inner surface 69 of body 65', which in turn is in fluid/material communication with inner channels 831, 832, 833. Inner channels 831, 832, 833 may be attached to said inner ring lumen or integrated with inner ring lumen. Thus, a proximal fluid/material source and port 8203 may be in fluid/material communication with inner channels 831, 832, 833, via said inner ring lumen and hub channel 8201.

The manner in which shaft 60' may be used is similar as discussed above for shaft 60, except a user may also adjust the diameter of central lumen 63' prior to or after the insertion of shaft 60' into a natural orifice and body lumen.

To inflate channels 831, 832, 833, the user may, for example, turn on a fluid/material source coupled to third hub 820, so that said fluid/material may pass through third hub 820 and an inner ring lumen, and flow into channels 831, 832, 833.

Figure 5A:
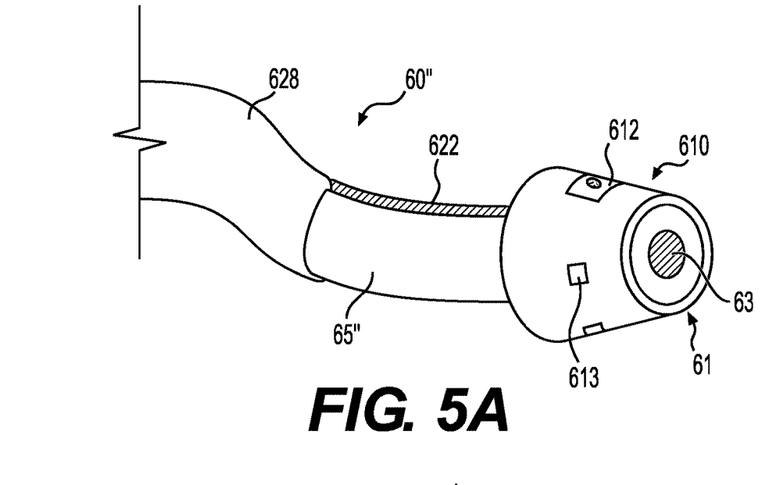
FIGS. 5A-5C are perspective views of a portion of another medical device, according to some aspects of the disclosure.
Figure 5B:
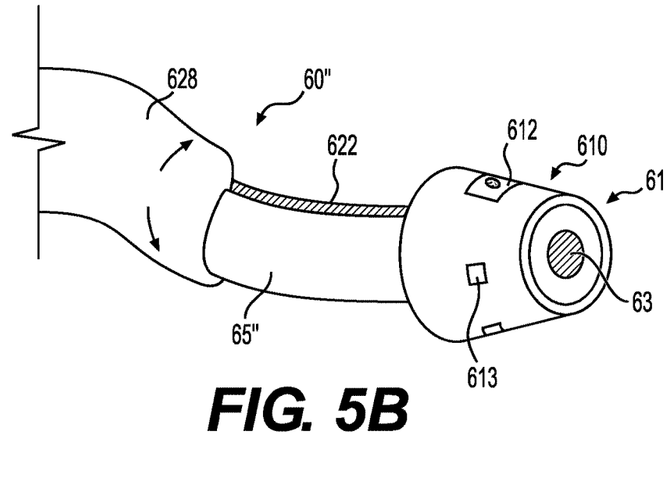
Figure 5C:
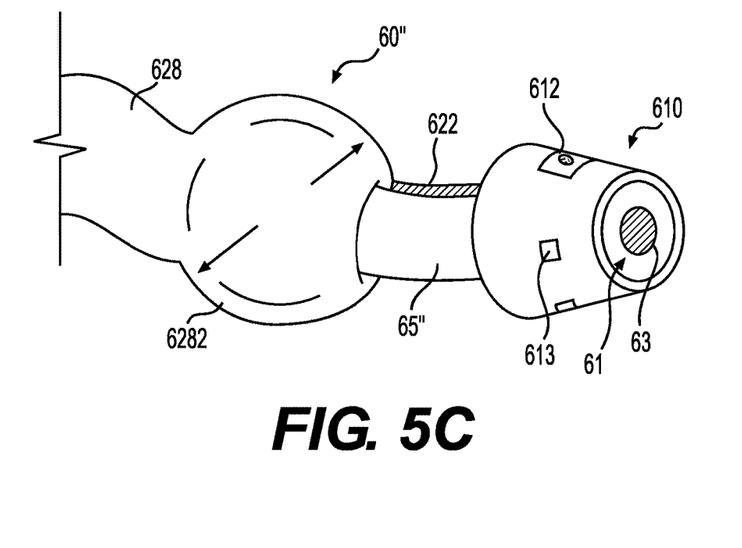

FIGS. 5A-5C illustrate another exemplary shaft 60". Unlike shafts 60, 60', body 65" of shaft 60" defines an inflatable sheath 628. Sheath 628 extends longitudinally along an outer surface of body 65", thereby defining at least a portion of the outer surface and the outer diameter of shaft 60". In shaft 60", sheath 628 defines a cavity (not shown) between an inner surface of sheath 628 and the outer surface of body 65", thereby defining an annular channel or passage extending between a proximal and distal end of sheath 628. It is noted that, in other embodiments, the shaft may also define second channels, e.g., 624, 626, and a flexible sheath may surround and cover the second channels so that the sheath may flex and expand with the inflation of the covered second channels. Regarding shaft 60", the proximal end of sheath 628 may include a proximal opening (not shown) in fluid/material communication with a hub (not shown), like second hub 623 of FIG. 1. Apart from the proximal opening, the proximal end of sheath 628 may otherwise be attached to the outer surface of body 65", thereby sealing the proximal end of sheath 628 to shaft body 65".

Shaft body 65" may also define first channel 622, in the same manner as shaft body 65. Thus, the distal end of first channel 622 may be in fluid/material communication with inflatable imaging module 610. Sheath 628 may surround and cover a portion of first channel 622 proximal to imaging module 610. As a result, the distal end of sheath 628 may be attached to the outer surface of body 65" as well as the surface of first channel 622, thereby sealing the distal end and forming an enclosed cavity that may receive and hold fluid/material.

The means by which said proximal and distal ends are attached to body 65" is not particularly limited, e.g., adhesives, overmolding. As noted above, sheath 628 may define an enclosed annular channel or passage configured to receive fluid/material, via second hub 623. As said enclosed annular channel receives fluid/material, sheath 628 may inflate from a default, deflated state (shown in FIG. 5A), and the outer diameter of shaft 60" may increase from a default diameter, e.g., any of the diameters discussed in this disclosure, to an adjusted diameter, as sheath 628 increasingly protrudes radially outwards relative to the outer surface of body 65" (shown in FIG. 5B).

Sheath 628 may further include a ballooning distal portion 6282. With further fluid/material provided to sheath 628, said distal portion 6282 may be configured to balloon and expand further radially outwards, relative to a remaining proximal portion of sheath 628. Distal portion 6282 may be further inflatable by any suitable means. For example, distal portion 6282 may be of a more elastic material, or may have less thickness than a remaining proximal portion of sheath 628. Distal portion 6282 may be a compliant or non-compliant balloon. Ballooned distal portion 6282 may provide additional stability and an anchoring feature to shaft 60". For example, ballooned distal portion 6282 may provide stability by minimizing or eliminating the gap between shaft 60" and surrounding tissue defining the bodily lumen. As a result, any room for radial displacement or movement of the shaft within the bodily lumen is minimized or eliminated. Ballooned distal portion 6282 may be inflatable to a size sufficient to anchor portion 6282 to a location within a bodily lumen.

It is noted that shaft 60" is not limited to the above disclosure, and may be further modified. In another exemplary embodiment, shaft 60" may further comprise individual longitudinal strips extending along at least a length of body 65", each strip functioning as a substitute for a steering cable/wire. Each of the longitudinal strips may extend from a distal end of shaft body 65" to a proximal end coupled to an actuating mechanism within the handle (not shown). Each of the individual longitudinal strips may be coupled to the distal portion of shaft body 65", but separated from a remaining portion of shaft body 65". Thus, the pulling of a longitudinal strip via the actuating mechanism of the handle may articulate a distal portion of shaft 60" in one direction. The longitudinal strips may be circumferentially arranged around body 65". For example, four strips may be placed 90° apart around body 65", thereby providing four degrees of freedom to a distal portion of shaft 65", e.g., up, down, left, and right. In this embodiment, sheath 628 may surround and cover at least a portion of the strips proximal to the distal, articulating portion of body 65". Longitudinal strips may be more advantageous than conventional steering cables/wires in that additional lumens within body 65" for receiving steering cables would not be necessary, and the guidance of cables through the aforementioned lumens would not be needed as well.

The manner in which shaft 60" may be used is similar as discussed above for shaft 60, except a user will be inflating sheath 628 instead of second channels 624, 626. A user may also further inflate sheath 628 so that distal portion 6282 may balloon to a preferred degree.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a handle;
   a shaft extending from the handle; and
   an inflatable module at a distal portion of the shaft, the inflatable module including a camera,
   wherein the shaft includes a body defining a first channel extending between a first end configured to be in fluid communication with a fluid source, and a second end in fluid communication with the inflatable module,
   wherein inflation of the inflatable module via the first channel alters a viewing angle of the camera relative to an axis of the distal portion of the shaft, such that, when the inflatable module is in a deflated state, the camera faces radially outward relative to the axis of the distal portion of the shaft and, when the inflatable module is in an inflated state, the camera faces distally.

2. The medical device of claim 1, wherein the body of the shaft further defines at least one inflatable second channel extending between a first end configured to be in fluid communication with a second fluid source and a sealed second end, so that the at least one inflatable second channel increasingly protrudes radially outwards, relative to an adjacent exterior surface of the body, when inflated from a deflated state.

3. The medical device of claim 2, wherein the at least one inflatable second channel includes a plurality of second channels, wherein the plurality of second channels are circumferentially arranged around the body of the shaft.

4. The medical device of claim 1, wherein the first channel includes a default, deflated state.

5. The medical device of claim 2, wherein the first channel and the at least one inflatable second channel are tubular structures extending longitudinally along an exterior of the body.

6. The medical device of claim 1, wherein the inflatable module is ring-shaped and coupled around the distal portion of the shaft.

7. The medical device of claim 1, wherein the inflatable module is coupled to the shaft so that the inflatable module hinges about a distal end of the inflatable module as the inflatable module is inflated.

8. The medical device of claim 6, wherein, in the deflated state of the inflatable module, a camera viewing angle is perpendicular to the axis of the distal portion of the shaft, and wherein, in the inflated state of the inflatable module, the camera viewing is parallel to the axis of the distal portion of the shaft.

9. The medical device of claim 8, wherein the inflatable module further includes a partially-inflated state, in which the camera viewing angle is at an angle between the camera viewing angle in the deflated state and the camera viewing angle in the inflated state.

10. The medical device of claim 2, further comprising a first intermediary hub including a first end and a second end, wherein the first end is configured to be coupled to a fluid source and the second end is configured to be coupled to the first end of the first channel.

11. The medical device of claim 10, further comprising a second intermediary hub including a first end configured to be coupled to the second fluid source and a second end in fluid communication with the at least one inflatable second channel.

12. The medical device of claim 1, further comprising a ring coupled to a proximal portion of the shaft, wherein the ring is translatable along the shaft when a force is applied by a user.

13. The medical device of claim 12, wherein the ring protrudes radially outwards relative to an exterior of the body of the shaft, and the ring frictionally engages the shaft to inhibit insertion of the shaft past the ring when inserting the shaft into an opening.

14. The medical device of claim 2, wherein a distal portion of the at least one inflatable second channel includes an enlarged portion that inflates to a cross-sectional dimension larger than a cross-sectional dimension of inflatable portions of the at least one inflatable second channel adjacent to the enlarged portion.

15. The medical device of claim 1, wherein the inflatable module is removable from the distal portion of the shaft.

16. A medical device, comprising:
a handle;
a shaft extending from the handle; and
an inflatable module coupled at a distal portion of the shaft, the inflatable module including a camera,
wherein the shaft includes a first channel, a working channel, and an inflatable annular channel surrounding the working channel,
wherein the first channel extends between a first end configured to be in fluid communication with a first fluid source, and a second end in fluid communication with the inflatable module,
wherein the inflatable annular channel extends between a first end configured to be in fluid communication with a second fluid source and a sealed second end, and
wherein the inflatable module includes a deflated state, in which a camera viewing angle is radially outward and perpendicular to an axis of the distal portion of the shaft, and an inflated state in which the camera viewing angle is parallel to the axis of the distal portion of the shaft.

17. The medical device of claim 16, wherein the inflatable annular channel is defined by a sheath encapsulating at least a portion of the shaft.

* * * * *